United States Patent
Musho et al.

(10) Patent No.: US 6,830,668 B2
(45) Date of Patent: Dec. 14, 2004

(54) SMALL VOLUME ELECTROCHEMICAL SENSOR

(75) Inventors: Matthew K. Musho, York, PA (US); Ronald E. Reed, York, PA (US); Donald L. Bohn, Boiling Springs, PA (US)

(73) Assignee: Conductive Technologies, Inc., York, PA (US)

( * ) Notice: Subject to any disclaimer, the term of this patent is extended or adjusted under 35 U.S.C. 154(b) by 346 days.

(21) Appl. No.: 10/134,478

(22) Filed: Apr. 30, 2002

(65) Prior Publication Data
US 2003/0201175 A1 Oct. 30, 2003

(51) Int. Cl.[7] .................... G01N 27/403; G01N 27/327; G01N 27/333; G01N 27/28
(52) U.S. Cl. .................. 204/400; 204/403.01; 204/416; 324/450
(58) Field of Search ..................... 204/403.01, 403.03, 204/403.14, 416, 409, 411, 412; 324/445, 446, 449, 450

(56) References Cited

U.S. PATENT DOCUMENTS

| | | |
|---|---|---|
| 4,420,564 A | 12/1983 | Tsuji et al. |
| 4,511,659 A | 4/1985 | Matson |
| 4,655,880 A | 4/1987 | Liu |
| 5,137,827 A | 8/1992 | Mroczkowski et al. |
| 5,250,439 A | 10/1993 | Musho et al. |
| 5,385,846 A | 1/1995 | Kuhn et al. |
| 5,512,489 A | 4/1996 | Girault et al. |
| 5,571,401 A | 11/1996 | Lewis et al. |
| 5,739,039 A | 4/1998 | Girault et al. |
| 5,788,833 A | 8/1998 | Lewis et al. |
| 5,911,872 A | 6/1999 | Lewis et al. |
| 5,916,156 A | 6/1999 | Hildenbrand et al. |
| 6,093,308 A | 7/2000 | Lewis et al. |
| 6,123,820 A * | 9/2000 | Bergkuist et al. ............ 204/411 |
| 6,210,972 B1 | 4/2001 | Williams et al. |
| 6,331,244 B1 | 12/2001 | Lewis et al. |
| 6,699,382 B2 * | 3/2004 | Yoshioka et al. ........ 205/777.5 |

* cited by examiner

Primary Examiner—Alex Noguerola
(74) Attorney, Agent, or Firm—Birch, Stewart, Kolasch & Birch, LLP

(57) ABSTRACT

An electrochemical sensor is provided comprised of a thin sheet or film having at least one through-hole provided therein. The thin sheet or film has first and second opposing surfaces, at least a portion of the opposing surfaces being coated with a conductive coating which extends into the at least one through-hole, each conductive coating extending partially into the at least one through-hole from each opposing surface whereby each conductive coating terminates within the at least one through-hole at a point spaced from the terminus of the opposing conductive coating which extends into the at least one through-hole, whereby the conductive coatings in the at least one through-hole are separated by a non-conductive interior surface of the at least one through-hole.

12 Claims, 4 Drawing Sheets

SMALL VOLUME ELECTROCHEMICAL SENSOR

BACKGROUND OF THE PRESENT INVENTION

Electrochemical sensors are known which are used in the analysis of liquid samples. Such sensors are used in the analysis of blood or other biological fluids.

For example, blood sugar analyzers analyze the blood sugar content or glucose concentration of a blood specimen by supplying a blood specimen to a fixed enzyme membrane to cause a chemical reaction. A reaction current is then generated proportional to the amount of the blood sugar in the blood specimen.

A person may also become infected with a disease, which will result in the person's blood containing measurable levels of an antigen specific to the disease. Immunodiagnostic tests are conducted on a sample of the infected person's blood whereby antibodies specific to the disease condition are contacted with the blood sample. If an antigen-antibody reaction occurs, the antigen is confirmed to be present. Of course, the reaction may be conducted in the reverse, by contacting an antigen with a sample containing the suspected antibody. While a variety of techniques have been developed to determine the result of the test (enzyme immunoassay, immunofluoresence, radioimmunoassay, etc.). It has also become appropriate to employ electrical immunoassay techniques whereby the electrical properties of the fluid sample are changed due to the antigen-antibody reaction. Alternatively, one immunoreactant can be labelled with an electroactive substance, with the extent of the reaction determining the level of the electrical property to be observed.

The above techniques, as well as several others, are described in U.S. Pat. No. 4,420,564 (blood sugar analyzer); U.S. Pat. No. 4,511,659 (liquid chromatograph with electrochemical detector); U.S. Pat. No. 4,655,880 (sensor apparatus using oxidase); U.S. Pat. No. 5,137,827 (diagnostic element for electrical detection of binding reaction); U.S. Pat. No. 5,250,439 (conductive sensor in diagnostic assay); U.S. Pat. No. 5,385,846 (biosensor for hematocrit determination); U.S. Pat. No. 5,512,489 (microelectrodes and amperometric assay); U.S. Pat. No. 5,571,401 (sensor arrays for detecting analytes in fluids); U.S. Pat. No. 5,739,039 (microelectrodes and amperometric assays); U.S. Pat. No. 5,788,833 (sensors for detecting analytes in fluids); U.S. Pat. No. 5,789,255 (blood glucose strips having reduced sensitivity to hematocrit); U.S. Pat. No. 5,911,872 (sensors for detecting analytes in fluids); U.S. Pat. No. 5,916,156 (electrochemical sensors having improved selectivity and enhanced sensitivity); U.S. Pat. No. 6,093,308 (sensors for detecting analytes in fluids); U.S. Pat. No. 6,210,972 (characterization of flowing dispersions); and U.S. Pat. No. 6,331,244 (sensors for detecting analytes in fluids).

Electrochemical sensors that require an ultra-small sample volume are of interest for those applications where the sample is difficult to produce or where the sample is recovered by invasive means which may involve the undesirable infliction of pain (such as penetration of the skin with a pointed object). Currently, it is believed that the smallest volume of liquid sample which can be analyzed is approximately 300 nL in size. Such devices are inherently planar in configuration, and draw a liquid sample into a single, large lateral flow transport channel. The configuration of the channel is based on several parameters, including material thickness, printed feature size and channel orientation. It is, however, desirable to produce an electrochemical sensor which enables liquid samples of much smaller volume to be analyzed.

OBJECTS AND SUMMARY OF THE INVENTION

It is accordingly an object of the present invention to provide an electrochemical sensor which may be used to perform small volume analysis of liquid samples such as biological fluids.

In accordance with the present invention, there is thus provided an electrochemical sensor comprised of a thin sheet or film having at least one through-hole provided therein, said thin sheet or film having first and second opposing surfaces, at least a portion of said opposing surfaces being coated with a conductive coating which extends into said at least one through-hole, each said conductive coating extending partially into said at least one through-hole from each opposing surface whereby each said conductive coating terminates within said at least one through-hole at a point spaced from the terminus of the opposing conductive coating which extends into said at least one through-hole, whereby said conductive coatings in said at least one through-hole are separated by an uncoated surface of said at least one through-hole.

DETAILED DESCRIPTION OF THE PRESENT INVENTION

Figure 1:
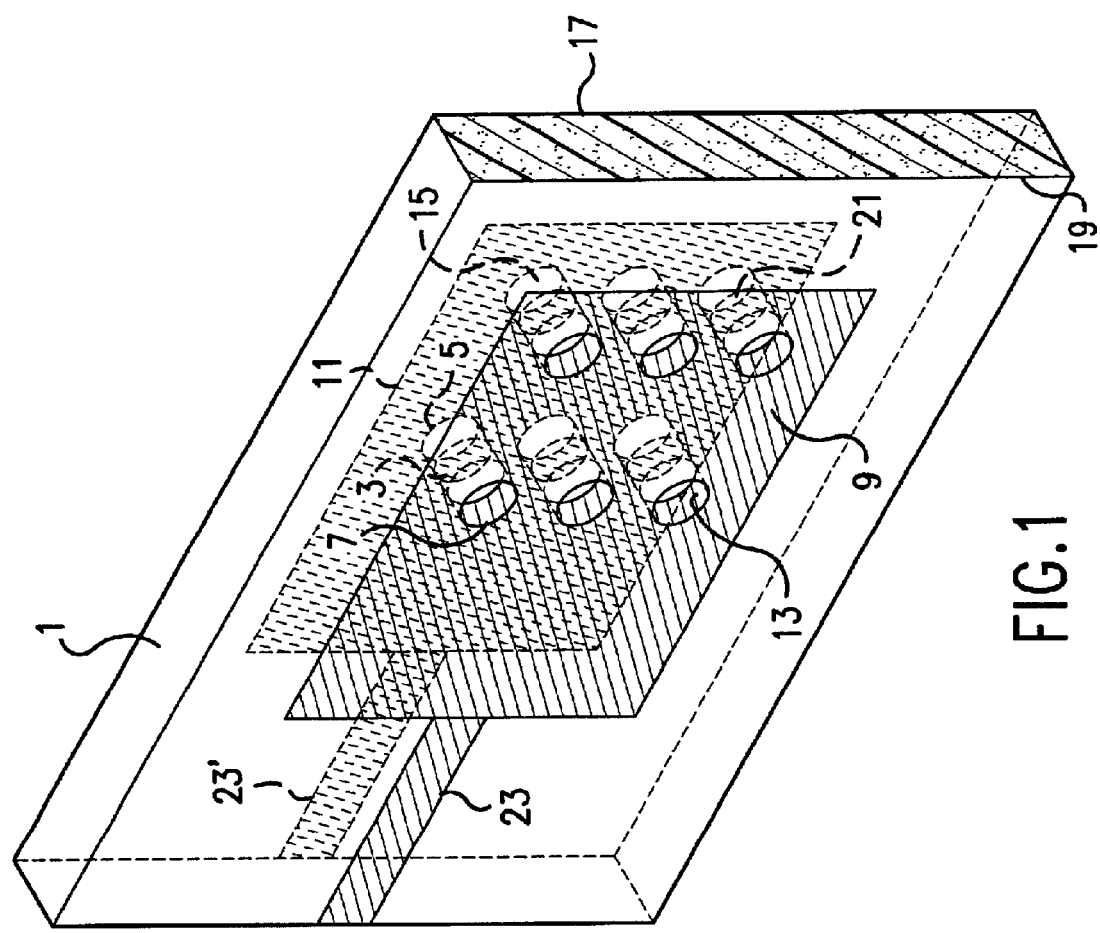
FIG. 1 is a view in perspective of an electrochemical sensor of the present invention.

The present invention is directed to an electrochemical sensor device which may be employed in the analysis of ultra-small liquid samples (on the order of >15 nL). The electrochemical sensor of the present invention enables analysis of liquid samples (such as biological samples) under circumstances where (1) a large volume sample is not available or impractical to obtain, and/or (2) the collection of the liquid sample requires uncomfortable or painful invasive procedures such as puncturing the skin of a person to draw blood.

The present invention addresses such issues by use of an electrochemical sensor comprised of at least one through-hole in a sheet or film in conjunction with a conductive coating on opposing surfaces of the sheet or film which coating extends partially into the through-hole. Upon contact of the surface of the sheet or film with a fluid to be analyzed, the fluid will enter the through-hole and complete the circuit between the opposing conductive coatings. An appropriate analysis of the fluid can then be conducted consistent with the electrochemical nature of the fluid and the coatings. As the sensor requires only small volumes of liquid sample for analysis, the collection of the sample from a patient may be rendered less intrusive.

By way of example, the electrochemical sensor of the present invention permits the detection, measurement or monitoring of an analyte in a liquid test sample, such as by oxidase chemistry. Glucose, cholesterol, alcohol as well as other analytes capable of reacting with a suitable oxidase enzyme can be assayed by the method of the present invention.

The sheet or film may be either flexible or rigid in character. The sheet or film is preferably comprised of a film-forming synthetic resin. Exemplary synthetic resins include poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(arylenes), poly(oxides), poly(carbonates), poly(esters), poly(urethanes), poly(sulfonates), poly(siloxanes), poly(sulfides), poly(thioesters), poly(sulfones), poly(amides), poly(acetals), and mixtures thereof, etc. The above listing is not all-inclusive, and one of ordinary skill in the art can readily determine what type of material can be employed to form the sheet or film.

The sheet or film preferably contains at least one through-hole of a size within the range of from about 0.005 to 0.030 inches in diameter. The diameter of the hole is preferably sized to be proportionate to the thickness of the sheet or film, with the hole being sized to enable coating of the interior surface of the hole without being completely coated from both sides. Typically, the thickness of the sheet or film will range from about 0.005 to about 0.040 inches.

The configuration of the electrochemical sensor of the present invention minimizes the volume of fluid sample to be analyzed by taking advantage of capillary flow of the liquid sample into the through-holes of the sensor, as opposed to transport of the fluid along larger transport channels as may occur in lateral flow devices.

The electrochemical sensor of the present invention may be produced by forming at least one through-hole in a sheet or film having a diameter within the stated range. The number of through-holes produced in the sheet or film is not critical. The number of through-holes may range from a single hole to a multitude of holes. However, the expected signal level from the liquid analysis can be increased by providing an array of through-holes, whereby each through-hole which contacts the liquid will contribute to the signal level which is produced. The respective through-holes may be formed by a variety of means, with the preferred means being by application of laser energy in order to provide a large number of consistently-size through-holes of desired spacing and diameter.

The spacing of the through-holes in the sheet or film is also not critical. However, the through-holes should be spaced and positioned in a manner which permits the desired number of through-holes to contact the fluid sample to be analyzed (i.e., the through-holes should be positioned within a transport path of the fluid if such a transport path resides along the surface of the sheet or film). For a through-hole having a diameter of approximately 0.010 inches with a sheet or film having a thickness of 0.005 inches, the sample volume within the through-hole is approximately 18 nL, well below the liquid sample volumes normally encountered in the prior art. Typically, the volume of the holes will range from about 1 to about 500 nL.

With the above in mind, the multitude of through-holes may take a variety of configurations. A variable array configuration may be employed, from a single through-hole to a large number of through-holes (limited only by the size of the sheet or film). As discussed above, the signal amplification is directly proportional to the number of holes which form the electrochemical cell. The respective through-holes may also be patterned as desired. For example, in order to enhance the signal from a particular analysis, the holes may be provided in pairs or greater numbers for a particular cell of the sensor. A single through-hole having an elongated slot configuration may also be used to maximize signal output by providing increased surface area for contact with the liquid sample. Different patterns or groupings of through-holes may comprise different electrochemical sensors within the same sheet or film, with a different analysis being capable of being conducted for each separate grouping of through-holes for a single liquid sample. In this regard, the composition of the electrode material may be varied among the groupings of through-holes, such that different ligands, analytes or complexing agents may be provided with different groupings of through-holes to enable such differing analysis to occur.

The diameters and configuration of holes may also be varied if deemed desirable. For instance, while it has been found that holes of a circular cross-section are highly satisfactory, the holes may also have other configurations. For example, the holes may be oblong or slit-like in configuration. The cross-sectional dimension of the hole should be sized such that, when a conductive coating is applied to the surface of the sheet or film on top of the hole, the coating is not caused to coat the entire inner surface of the hole (due either to the hole being so large that the coating "falls into the hole" or so small that the hole is so small as to cause the interior of the hole to be completely filled due to capillary action). Whether such undesirable complete coating of the interior of the hole occurs depends not only on the dimensions of the hole, but also on the viscosity of the conductive coating to be applied to the surface of the sheet or film.

Once the sheet or film is provided with at least one through-hole, a conductive liquid (such as a conductive ink) is applied to the surface of the sheet or film in a manner which covers the at least one through-holes. The same or different conductive liquid can be applied to the opposing surfaces of the sheet or film. The conductive liquid is caused by capillary action to coat a portion of the inner surface of the through-hole extending from the edge of the hole partially into the interior of the hole. The conductive liquid (either the same or different) extends from each opposing surface of the through-hole partially into the interior of the hole. Each coating terminates short of the opposing coating within the hole, such that a non-coated non-conductive portion of the inner surface of the hole separates the respective coated surfaces. The distance between the respective terminal points of the opposing coatings within the hole is not critical. However, the distance between the respective coatings in the hole must be sufficient to ensure that no electrical contact occurs between the respective coatings prior to the analysis of the liquid sample.

The composition of the conductive fluid is not critical. It is important, however, that the conductive fluid be able to dry upon being coated on the sheet or film, leaving a conductive coating thereon. Exemplary conductive fluids include solvated polymer solutions containing conductive particles such as carbon, silver, gold, copper, etc., as well as mixtures thereof. The conductive solids content of the solvated polymer will generally range from about 40 to 90% by weight, based on the total weight of the solvent, polymer and conductive solids in the mixture. The amount of conductive particles required to be present in the mixture to provide the desired electrical conductivity may vary depending upon the identity of the conductive particle due to differences among the particles with respect to density, conductivity, etc. It is not necessary that the conductive coating applied to the opposing sides of the sheet or film be the same coating, as different coatings may be applied to each side.

The conductive coating may be comprised of a variety of film-forming polymers which are compatible with the conductive particles admixed therewith and which will adhere to the sheet or film upon removal of the solvent. Exemplary film-forming polymers which may be used to form the conductive coating include but are not limited to a variety of polymers such as polyesters and polyacrylates, etc. One of ordinary skill in the art can readily ascertain the identity of acceptable polymers for use in the conductive coating.

The consistency of the conductive coating as applied to the sheet or film is desirably "paste-like" in order to permit coating of the sheet or film in a manner which encourages partial coating of the inside of the holes. Typically, the viscosity of the conductive coating upon application will range from about 25,000 to about 80,000 cps. The coating may be applied by any conventional means such as by knife coating. Once applied, solvent contained in the coating is removed by any conventional method, such as by exposure of the coated sheet or film to elevated temperatures sufficient to removed the solvent and yield a dried coating. However, the elevated temperature employed cannot be so elevated as to adversely affect the physical stability of the sheet or film. Typically, the elevated temperatures employed to removed the solvent present in the coating ranges from about ambient to about 290° F., and preferably in the range of from about 220 to about 280° F. Once the solvent is removed, a dried conductive coating is formed of the desired configuration. In this regard, the conductive coating on the surface of the sheet or film may take many configurations.

For instance, the at least one hole may be electrically connected by providing an elongated strip of conductive coating over the at least one hole on each opposing side of the sheet or film. Electrical "leads" (in the form of the conductive coating) may also be provided extending from an elongated strip of conductive coating on each opposing surface of the sheet or film. Such "leads" may be placed into contact with a suitable analyzer to monitor electrical properties of the sensor upon application of a liquid sample to the sensor. The "leads" may also be either on both sides of the sheet or film, or on the same side. If on the same side, one lead(s) may extend from an opposing side to a common side by providing a hole which has been sufficiently coated on the inside of the hole to permit electrical contact from one set of leads through the sheet or film to the opposing side.

Once the sheet or film is provided with a conductive coating in the manner discussed above, a reagent layer may be provided which is specific to the type of fluid analysis desired to be conducted. For example, the reagent layer may be comprised of an enzyme, an ionotophore, an antibody or any other agent that lends specificity to the analysis when a fluid sample to be analyzed contacts the sheet or film adjacent the multitude of through-holes. The reagent layer may be coated on one of the opposing surfaces of the sheet or film (which surface initially contacts the liquid sample) and/or coated on at least a portion of the interior surface of at least a portion of the holes. Different reagents may be applied to different holes or sets of holes to permit different types of analyses to occur for a single sensor.

It may also be useful to provide a dielectric coating over various portions of the sheet or film to electrically insulate such portions of the coated sheet or film. Such coatings are well known to those skilled in the art and may comprise, for example, urethanes, acrylates, polyesters, etc.

The electrochemical sensor of the present invention discussed above is depicted in FIGS. 1 to 4, with like numerals depicting like elements in the drawings.

As shown in FIG. 1, a sheet or film 1 is provided with a multitude of through-holes 3 which extend completely through the sheet or film providing communication between the opposing surfaces 17, 19 through respective openings 5, 7 in the opposing surfaces of the sheet or film. Opposing surfaces 17, 19 are coated with a conductive coating 9, 11 over a surface that is coextensive with the through-holes. The respective coatings 9, 11 extend into the respective openings of the through-holes resulting in coatings 13, 15 on the interior surface of the through-holes, leaving uncoated surfaces 21 serving as electrically non-conductive barriers between coatings 13, 15. In order to permit the electrochemical cell to be used for analysis of the liquid sample, electrodes 23, 23' are in communication with the conductive surface portion 9, 11 of each opposing surface 17, 19. The electrodes are also placed in communication with a suitable diagnostic device (not shown) which permits analysis of the electrochemical activity of the liquid sample once it contacts one of surfaces 9, 11 and enters the through-holes 3. The electrodes as shown in FIG. 1 may simply be comprised of extensions of the conductive coatings 9, 11.

Figure 2:
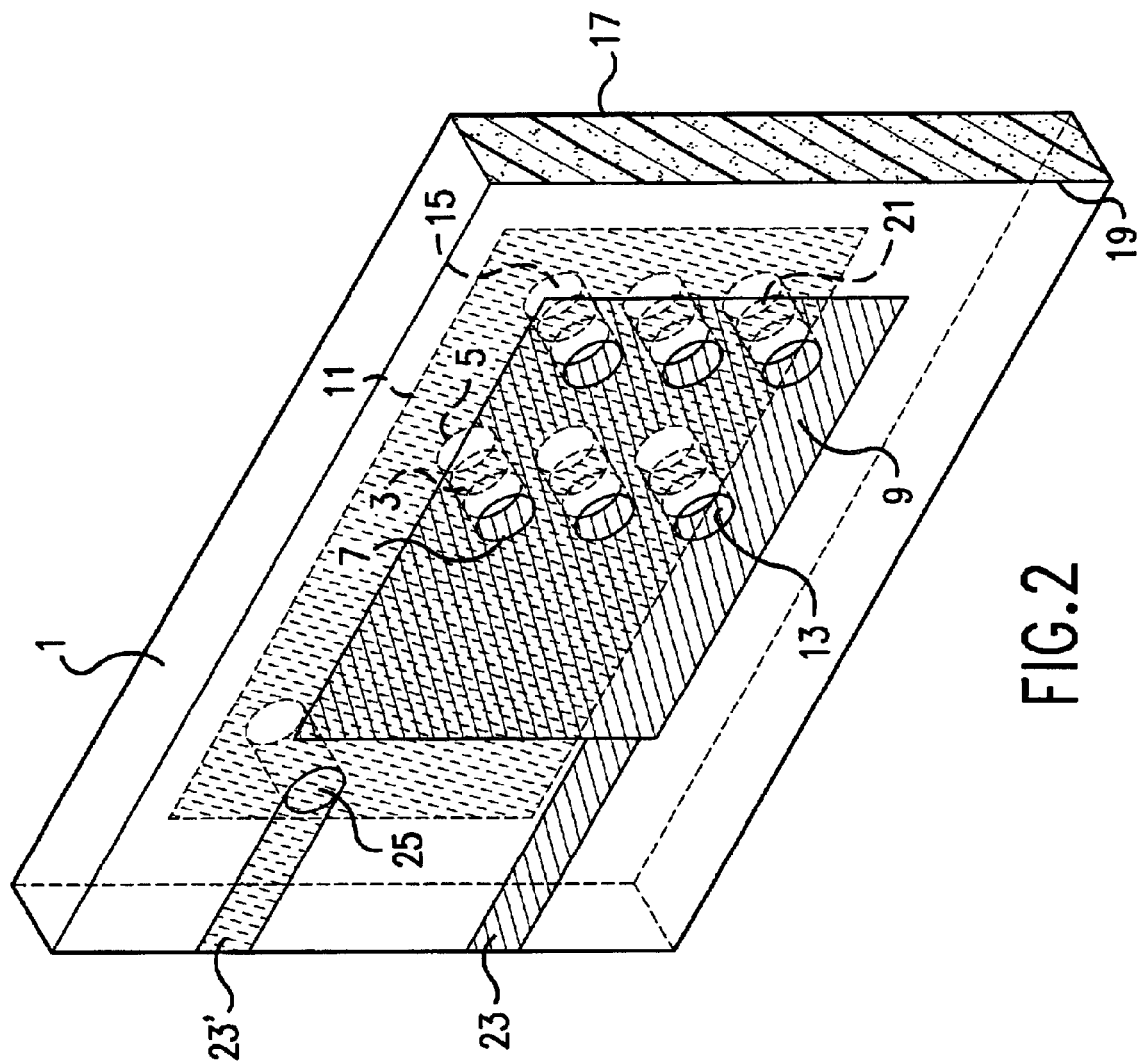
FIG. 2 is a view is perspective of another embodiment of the electrochemical sensor of the present invention.

In an alternative embodiment as shown in FIG. 2, the electrodes 23, 23' may be formed on the same side of the sheet or film. In such an embodiment, electrode 23' is electrically connected to conductive coating 11 through a through-hole 25 which is coated on its interior surface sufficiently throughout the hole to provide electrical connection between the opposing surfaces 9, 11 upon contact of the liquid sample with the remaining holes. Preferably, the entire interior surface of hole 25 is coated with the conductive coating.

Figure 3:
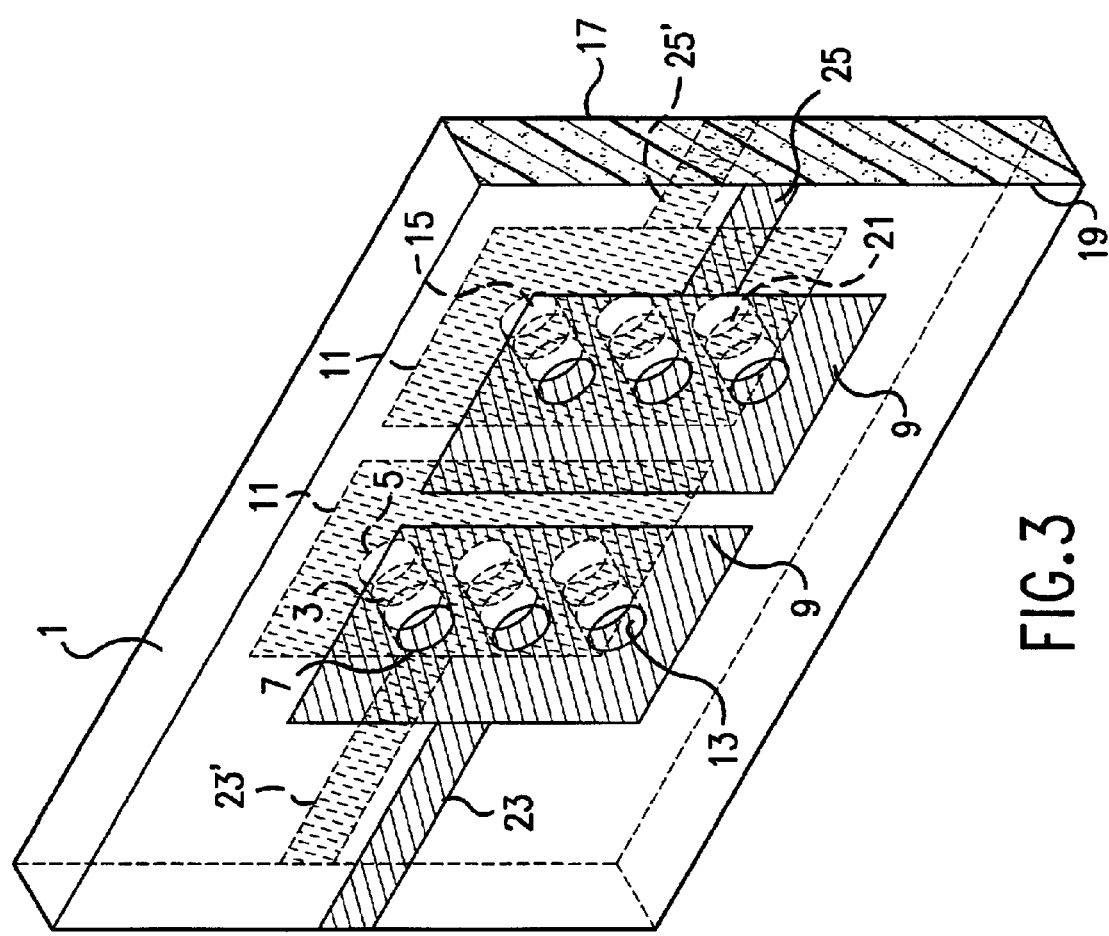
FIG. 3 is a view in perspective of another embodiment of the electrochemical sensor of the present invention.
Figure 4:
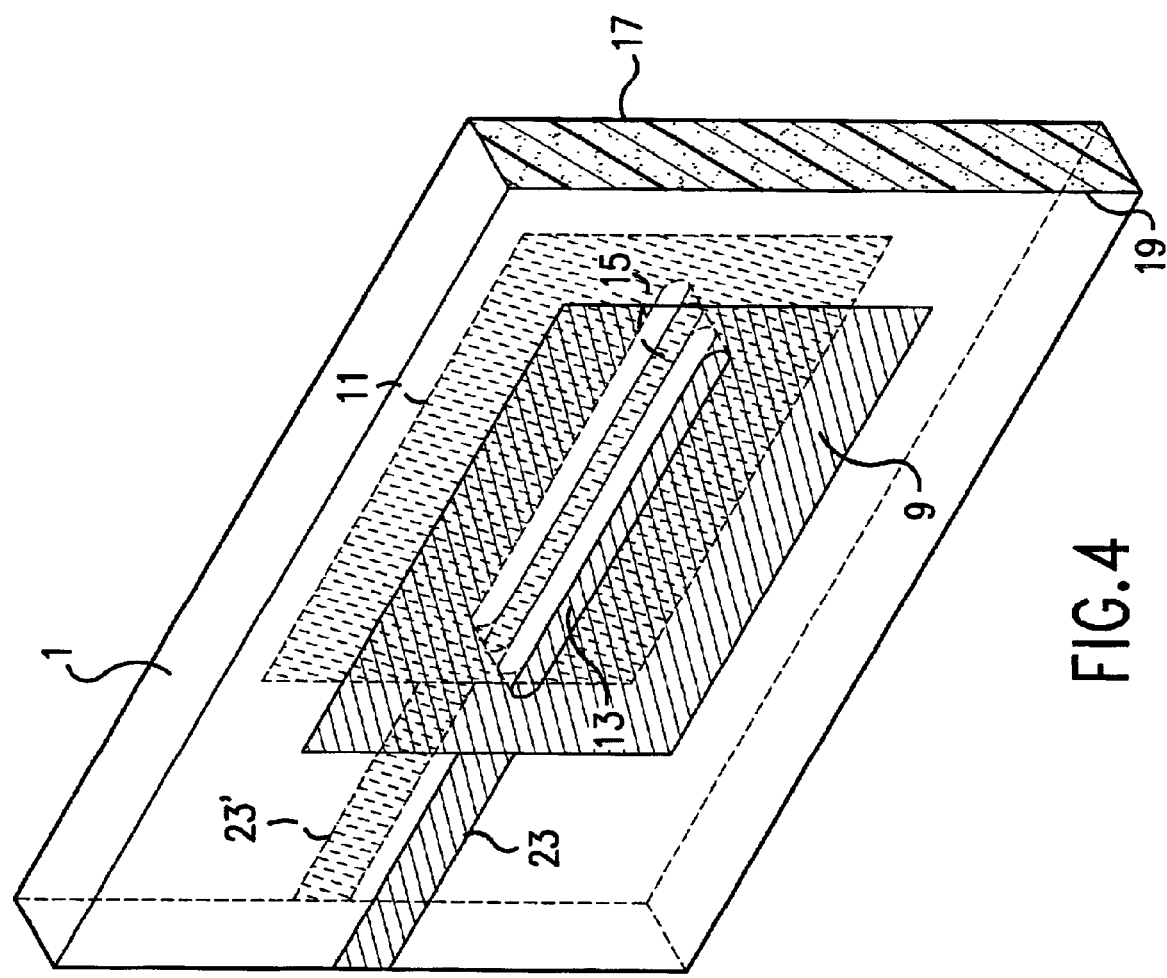
FIG. 4 is a view in perspective of another embodiment of the electrochemical sensor of the present invention.

In the event that different groupings of the holes 3 are dedicated to different types of analysis of the liquid sample, then multiple electrodes would be attached to the sheet or film, each dedicated to a particular set of through-holes as shown in FIG. 3. In such an instance, coatings 9, 11 would not be coextensive along the respective surfaces, but would be limited in area to those groups of holes dedicated to each particular analysis. In such an instance, different application points would be provided for the liquid sample to ensure separate application to the different groups of holes to permit the desired different types of analysis of the liquid. Different sets of leads 23, 23' and 25, 25' are provided which may be connected to separate analysis means (not shown). FIG. 4 depicts an embodiment wherein only a single through-hole is employed, but which is in the form of an elongated slot.

The sensor 1 is preferably employed in association with a housing (not shown), which housing encloses the sheet or film. The housing would include a port for supplying the liquid sample to be analyzed, as well as ports to permit the electrodes (not shown) to exit from the housing to be connected to a suitable analyzer.

What is claimed is:

1. An electrochemical sensor comprised of a thin sheet or film having at least one through-hole provided therein, said thin sheet or films having first and second opposing surfaces, at least a portion of each said opposing surface being coated with a polymeric conductive coating which extends into said at least one through-hole, each said polymeric conductive coating extending partially into said at least one through-hole from each opposing surface whereby each said polymeric conductive coating terminates within said at least one through-hole at a point spaced from the terminus of the opposing polymeric conductive coating which extends into said at least one through-hole, whereby said polymeric conductive coatings in said at least one through-hole are separated by a non-conductive interior surface of said at least one through-hole.

2. The sensor of claim 1, wherein said sheet or film is comprised of a non-conductive synthetic resin.

3. The sensor of claim 1, wherein said sheet or film has a thickness within the range of about 0.005 to about 0.040 inches.

4. The sensor of claim 1, wherein said at least one through-hole has a diameter within the range of about 0.005 to about 0.030 inches.

5. The sensor of claim 1, wherein said polymeric conductive coating comprises conductive particles.

6. The sensor of claim 5, wherein said conductive particles are selected from the group consisting of carbon, silver, gold, and copper particles and mixtures thereof.

7. The sensor of claim 1, wherein said sensor comprises a multitude of through-holes.

8. The sensor of claim 7, comprising a multitude of through-holes arranged in at least two separate groups on said sheet or film, with each group being connected to separate electrical leads.

9. The sensor of claim 1, wherein said at least one through-hole has a volume within the range of from about 1 to about 500 nL.

10. The sensor of claim 1, further comprising electrodes electrically connected to the polymeric conductive coating on each opposing surface.

11. The sensor of claim 1, wherein said at least one through-hole has a slot-like configuration.

12. The sensor of claim 1, wherein at least a portion of said polymeric conductive coating is coated with an electrically insulating material.

* * * * *